United States Patent [19]

Ogawa et al.

[11] Patent Number: 6,071,859

[45] Date of Patent: Jun. 6, 2000

[54] RED TIDE ELIMINATING COMPOSITION AND METHOD FOR GETTING RID OF RED TIDE

[75] Inventors: Yasuaki Ogawa, Uji; Kenji Uemura, Nara, both of Japan; Mikio Nakanishi, 2492-161 Hakonoura, Hannan-shi, Osaka 599-02, Japan

[73] Assignees: New Japan Chemical Co., Ltd., Kyoto; Mikio Nakanishi; Nichimen Corporation, both of Osaka, all of Japan

[21] Appl. No.: 09/171,179

[22] PCT Filed: Apr. 15, 1997

[86] PCT No.: PCT/JP97/01299

§ 371 Date: Oct. 14, 1998

§ 102(e) Date: Oct. 14, 1998

[87] PCT Pub. No.: WO97/38580

PCT Pub. Date: Oct. 23, 1997

[30] Foreign Application Priority Data

Apr. 15, 1996 [JP] Japan .................................. 8-118542

[51] Int. Cl.⁷ ........................... A01N 25/08; A01N 37/12
[52] U.S. Cl. ............................................. 504/151; 504/157
[58] Field of Search ...................................... 504/151, 157

[56] References Cited

FOREIGN PATENT DOCUMENTS

| | | |
|---|---|---|
| 50-123821 | 9/1975 | Japan . |
| 53-72362 | 6/1978 | Japan . |
| 57-119886 | 7/1982 | Japan . |
| 6-16504 | 1/1994 | Japan . |

*Primary Examiner*—S. Mark Clardy
*Attorney, Agent, or Firm*—Larson & Taylor PLC

[57] ABSTRACT

This invention provides a red tide eliminating composition comprising:

(a) at least one (polyoxyalkylene) fatty acid ester represented by the formula (1)

$$RCOO(AO)nH \qquad (1)$$

wherein R represents a $C_{7-22}$ alkyl or alkenyl group, n represents an integer of 1 to 30 and AO represents a $C_{2-4}$ alkylene oxide, and (b) at least one powdery adsorbent; wherein, based on the total weight of the above at least one (polyoxyalkylene) fatty acid ester (a) represented by the formula (1) and the above at least one adsorbent (b), the above at least one (polyoxyalkylene) fatty acid ester (a) represented by the formula (1) is present in an amount of 1 to 70 wt. % and the above at least one adsorbent (b) is present in an amount of 99 to 30 wt. %; and a method for eliminating red tide by use of the composition.

24 Claims, No Drawings

RED TIDE ELIMINATING COMPOSITION AND METHOD FOR GETTING RID OF RED TIDE

TECHNICAL FIELD

The present invention relates to red tide eliminating compositions, in particular controlled-release red tide eliminating compositions which disperse in a short period and at a uniform concentration and which have excellent red tide eliminating effect. The present invention also relates to methods for eliminating red tide.

BACKGROUND ART

Known methods for eliminating red tide include those using hydrogen peroxide (Suisan Zoshoku), 39 (2), 189–193 (1991)). However, the effects of these methods remain to be improved.

Colloidal particles of clay minerals possess a property of agglomerating and adsorbing suspended matter in the water, so that utilizing this property, clays are also used as red tide eliminating agents. Clays are basic units of soil constituting the earth, and thus can be found everywhere and readily available. Particles of clays are plate crystals and form various clay minerals because of the difference in the crystal lattices plate number of silicate and alumina, or substitution of metal ions. This difference in the structure result in different capabilities of eliminating organisms by absorption. Accordingly, usable clays are restricted in origin and species.

Also known are methods which uses surfactants. Examples of such surfactants include alkylbenzenesulfonates (ABS), linear alkylbenzenesulfonates (LAS) (Bulletin of Environmental Contamination & Technology, 18, (3), 291 (1977)), or salts of an alkyl ether sulfuric acid ester to be used in combination with natural extracts (Japanese Unexamined Patent Publication No. 66603/1991). However, ABS and LAS are inferior in respect of biodegradability, aquatic toxicity or hard water resistance, and thus are not preferable.

Generally, red tide eliminating compositions are required to have the following characteristics:
(1) being effective at a low concentration,
(2) having small adverse effect on fish, shellfish, seaweeds, etc.
(3) being capable of dispersing in a desired range in a short period when applied,
(4) being capable of uniformly dispersing in a desired range when applied,
(5) having small adverse effect on environment,
(6) being prepared from inexpensive, readily available materials, and
(7) being safe to handle and causing no problem in practical use.

These requirements are all important, but no red tide eliminating agent has been proposed so far which fully satisfies such problems.

DISCLOSURE OF THE INVENTION

An object of the present invention is to provide a novel and useful composition for eliminating red tide planktons, which is not only safe but also practically usable.

The red tide eliminating composition of the invention comprises 1 to 70 wt. % of a (polyoxyalkylene) fatty acid ester represented by the formula (1) (hereinafter referred to as "the present surfactant") and 99 to 30 wt. % of an adsorbent.

$$RCOO(AO)nH \quad (1)$$

wherein R represents a $C_{7-22}$, in particular $C_{8-22}$, alkyl or alkenyl group, n represents an integer of 1 to 30, and AO represents a $C_{2-4}$ alkylene oxide.

More specifically, the present invention provides a red tide eliminating composition comprising:
(a) at least one (polyoxyalkylene) fatty acid ester represented by the formula (1)

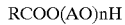

$$RCOO(AO)nH \quad (1)$$

wherein R represents a $C_{7-22}$, in particular $C_{8-22}$ alkyl or alkenyl group, n represents an integer of 1 to 30, and AO represents a $C_{2-4}$ alkylene oxide, and (b) at least one powdery adsorbent; wherein, based on the total amount of said at least one (polyoxyalkylene) fatty acid ester (a) represented by the formula (1) and said at least one adsorbent (b), said at least one (polyoxyalkylene) fatty acid ester (a) represented by the formula (1) is present in an amount of 1 to 70 wt. % and said at least one adsorbent (b) is present in an amount of 99 to 30 wt. %.

The present inventors prepared various red tide eliminating compositions in an attempt to solve the above problems, and carried out extensive research on their characteristics. Consequently, they found the following facts and accomplished the present invention based on these findings.

(1) A composition comprising a nonionic surfactant of the above-specified structure and an adsorbent as essential components, in which the essential components are present in the specific proportions, can effectively eliminate red tide planktons occurring in bodies of seawater, such as Chattonella, Gymnodinium, Heterosigma and the like, when applied to areas affected by such red tide planktons.

(2) The above eliminating composition diffuses and descends efficiently in the desired range of seawater or freshwater in a short time. Specifically, use of the surfactant improves wettability of the adsorbent particles and increases the rate of diffusion of the particles in the vertical direction, with the result that the composition can reach a desired depth of 4 to 7 m in a short time.

(3) The composition, when applied to seawater or freshwater, is uniformly dispersed and therefore is effective even at a low concentration. Specifically, use of the adsorbent enables controlled release of the surfactant and maintains the uniform concentration of the present surfactant even at a depth of about 5 m. Consequently, the use of a small amount of the red tide eliminating composition of the present invention can efficiently achieve the contemplated effect.

(4) The red tide plankton eliminating effect achieved by the composition of the present invention is synergistic, and is remarkably improved as compared with the effect of each component. That is, the contemplated effects can be achieved by using the composition in an amount smaller than the effective amount of the adsorbent as used singly. Similarly, a composition containing the surfactant alone cannot accomplish a uniform concentration dispersion which is important particularly for use in open systems, and causes a concentration gradient so that it remains to be largely improved in practical use.

(5) The present composition can minimize safety problems such as aquatic toxicity.

The composition of the invention will be described below in detail.

(a) (Polyoxyalkylene) fatty acid ester

According to the invention, the (polyoxyalkylene) fatty acid ester of the formula (1) is used as an essential component.

The nonionic surfactants of the formula (1) for use in the invention are known or can be prepared by adding a specified alkylene oxide to a specific fatty acid in a conventional manner.

The fatty acid constituting the surfactant of the formula (1) may be, for example, a $C_{8-23}$, in particular $C_{9-23}$, preferably $C_{12-18}$ saturated or unsaturated fatty acid. Particularly recommendable are various fatty acids such as caprylic acid, capric acid, lauric acid, myristic acid, palmitic acid, stearic acid, oleic acid, isostearic acid, behenic acid, coconut oil fatty acid, palm oil fatty acid, palm kernel oil fatty acid, beef tallow fatty acid, hydrogenated soybean or fish oil fatty acid, and the like.

Use of a polyunsaturated acid such as soybean fatty acid or fish oil fatty acid tends to impair stability with time and powder properties. Accordingly, when an unsaturated fatty acid is used, a preferred number of the double bonds in the fatty acid is generally about 1 to 2, but it is recommendable that the number of double bonds contained in the unsaturated fatty acid is 1, from the viewpoint of powder properties, such as caking-preventing property, of the resulting red tide eliminating composition.

Examples of alkylene oxides to be added to the above fatty acid include those having 2 to 4 carbon atoms, such as ethylene oxide (EO), propylene oxide (PO) and butylene oxide (BO). They may be used singly, or at least two of them may be used to undergo block or random co-addition.

The number of moles of the alkylene oxide to be added is usually 1 to 30 moles, preferably 7 to 20 moles. If the alkylene oxide is not added, no effect is achieved and there would be no water solubility. On the other hand, if more than 30 moles of the alkylene oxide is added, the red tide eliminating effect tends to markedly decrease. Hence amounts outside the specified range are not preferable.

Nonionic surfactants of the formula (1), wherein R has a longer chain length or the number of moles of AO added is greater than necessary, are not preferable since such surfactants have a high melting point and will not be sufficiently soluble in low-temperature sea areas, greatly diminishing the effect.

Accordingly, it is suitable that R has 7 to 22, in particular 8 to 22 carbon atoms, and that the number of moles of AO added is 1 to 30, as mentioned above.

The present surfactant can be prepared by esterifying a fatty acid with polyethylene glycol (having a molecular weight of, for example, 300 to 900). However, this esterification inevitably produces a diester as a by-product, in addition to the desired monoester. The resulting surfactant tends to have a slightly reduced performance, if containing a large amount of the by-product.

Of the surfactants represented by the formula (1), recommendable are ethylene oxide adducts of lauric acid, myristic acid, palmitic acid, oleic acid, isostearic acid or a mixture thereof (the number of moles added=1 to 30, preferably 7 to 20). Mixtures of these ethylene oxide adducts may also be used.

Also preferable are ethylene oxide adducts of coconut oil fatty acid (the number of moles of ethylene oxide added=1 to 30, preferably 7 to 20). Such adducts may be used singly or in combination with at least one of ;the above ethylene oxide adducts of lauric acid, myristic acid, palmitic acid, oleic acid, isostearic acid or a mixture thereof (the number of moles of ethylene oxide added=1 to 30, preferably 7 to 20).

When one or more EO adducts of a liquid fatty acid (such as EO adducts of oleic acid) are used singly or in the form of a mixture of at least two of them, as the (polyoxyethylene) fatty acid ester of the formula (1), the proportion of said one or more EO adducts can be suitably selected in view of the powder properties, in particular caking-preventing property, of the resulting red tide eliminating composition. For example, when an EO adduct of oleic acid is used singly, the proportion of the EO adduct of oleic acid is preferably 15 wt. % or less based on the total weight of the EO adduct of oleic acid and the adsorbent. When an EO adduct of oleic acid is used as mixed with one or more of the above EO adducts of saturated fatty acids, the proportion of the EO adduct of oleic acid is preferably 40 wt. % or less based on the mixture.

When two or more alkylene oxide adducts of fatty acids (such as lauric acid, myristic acid, palmitic acid, etc.) are used in admixture, they may be mixed in any ratio.

Examples of typical (polyoxyalkylene) fatty acid esters represented by the formula (1) include the following:

EO adduct of lauric acid (the number of moles of EO added=9)

EO adduct of myristic acid (the number of moles of EO added=12 or 14)

EO adduct of palmitic acid (the number of moles of EO added=14)

EO adduct of oleic acid (the number of moles of EO added=12 or 14)

EO adduct of coconut oil fatty acid (the number of moles of EO added=10)

Mixture of 70 wt. % of EO adduct of myristic acid (the number of moles of EO added=14) and 30 wt. % of EO adduct of oleic acid (the number of moles of EO added=14)

Mixture of 50 wt. % of EO adduct of lauric acid (the number of moles of EO added=9) and 50 wt. % of EO adduct of myristic acid(the number of moles of EO added=12)

The surfactant of the formula (1) may be used singly, but may also be used in combination with at least one other surfactants. Examples of other surfactants for combined use include the following:

salts of $C_{8-18}$ alkyl (or alkenyl) sulfuric acid esters salts of polyoxyethylene alkyl (or alkenyl) ($C_{6-18}$) ether sulfuric acid esters dodecylbenzenesulfonic acid salts salts of α-sulfofatty acid ($C_{8-18}$) esters $C_{10-18}$ α-olefin sulfonic acid salts $C_{8-18}$ alkyl (alkenyl) sulfonic acid salts polyoxyethylene (the number of moles of EO added=1–30) polyhydric alcohol fatty acid ($C_{8-18}$) esters, such as polyoxyethylene glycerine fatty acid ester, polyoxyethylene sorbitan fatty acid ester, polyoxyethylene pentaerythritol fatty acid ester, and the like polyhydric alcohol fatty acid ($C_{8-18}$) esters wherein the polyhydric alcohol is, for example, glycol, glycerine, sorbitol, mannitol, pentaerythritol, sucrose or the like Polyglycerine (polymerization degree=2–10) fatty acid ($C_{8-18}$) esters, such as tetraglycerine monostearate, hexaglycerine monolaurate, decaglycerine monostearate, or the like Polyoxyalkylene (the number of moles of alkylene oxide added=1–30) alkyl ($C_{8-36}$) ethers Polyoxyethylene-polyoxypropylene glycols (including block copolymers and random copolymers)

Polyoxyethylene-polyoxypropylene alkyl ($C_{8-18}$) ethers (including block copolymers and random copolymers)

Polyoxyalkylene (in particular polyoxyethylene, the number of moles of EO added=1–30) fatty acid ($C_{8-18}$) alkylolamides, such as ethylene oxide adducts of mono- or diethanol amides of lauric acid, oleic acid or coconut oil fatty acid Fatty acid ($C_{8-18}$) alkylolamides, such as mono- or diethanol amides of lauric acid, oleic acid and coconut oil fatty acid Polyoxyalkylene adducts of caster oil (the number of moles of alkylene oxide added=1–100, in particular 10–50)

Polyoxyalkylene (such as polyoxyethylene) alkyl (or alkenyl) amines wherein the number of moles of alkylene oxide added is 1 to 30 and the alkyl or alkenyl group has 8 to 36 carbon atoms, such as polyoxyethylene laurylamine, polyoxyethylene myristylamine and the like.

The salts forming the above surfactants for combined use include, for example, Na salt, Li salt, K salt, triethanolamine salt, ammonium salt and the like. The polyoxyalkylenes in the above examples include those derived from $C_{2-4}$ alkylene oxide adducts.

The above optional surfactants for combined use, when employed, is used in a proportion of about 5 to 200 wt. parts, more preferably about 10 to 100 wt. parts, in particular about 40 to 100 wt. parts, per 100 wt. parts of the surfactant of the formula (1).

(b) Adsorbent

Adsorbents to be used in the red tide eliminating composition of the present invention include acid clay, activated clay, silica alumina, synthetic zeolite, silicic acid, alkali metal salts of silicic acid (such as sodium silicate), aluminum silicate, aluminosilicate, activated alumina, silica, oil absorbing silica, diatomaceous earth and the like. They can be used singly or at least two of them may be used in admixture.

Particularly preferred adsorbents are activated clay, synthetic zeolite, oil absorbing silica or diatomaceous earth, or a mixture of 50 wt. % of synthetic zeolite and 50 wt. % of diatomaceous earth, or a mixture of 50 wt. % of activated clay and 50 wt. % of aluminum silicate.

The adsorbent is used in the red tide eliminating composition of the invention in expectation that the adsorbent will adsorb the surfactant in its pores, rather than destroy the cells of red tide planktons, thereby allowing the adsorbent particles to descend at a higher speed because of the wetting effect of the surfactant and to gradually release the surfactant while the adsorbent particles are descending.

For achieving the above effects, the specific gravity, particle size, surface area, pore size and oil absorbing property of the adsorbent are important factors. Particularly preferable are adsorbents having, among others, at least one physical property selected from the group consisting of a surface area within a certain range, a pore size within a certain range and an oil absorption within a certain range.

For practical use, adsorbents having at least one of the following physical properties are recommendable.

a) an oil absorption of 150 ml or more, preferably 160 to 250 ml, per 100 g of the adsorbent (as determined according to JIS K 6220–1977)

b) a specific surface area of 150 $m^2$/g or more, preferably 200 to 400 m /g, and c) a pore size of 3 to 100 angstroms, preferably 3 to 20 angstroms.

The adsorbent for use in the invention has at least one of the above physical properties a), b) and c), or may have two or three of them.

The descending speed of the adsorbent varies depending on its particle size. It descends slowly when having a small particle size and descends rapidly when having a large particle size. Accordingly, when planktons are localized at the surface of the seawater or freshwater, it is preferable that the particle size of the adsorbent is small. When the composition of the invention is intended to be sunk to a depth of about 7 m within a certain period of time, a larger particle size is desirable. Generally, the particle size of the adsorbent is suitably selected from the range of about 1 to 200 μm, preferably about 30 to 100 μm, according to the depth of the place to be treated with the red tide eliminating composition.

Typical examples of preferred adsorbents are given below. Adsorbents having a small particle size may be granulated into grains having a desired size, by conventional methods using a binder such as clay. Conversely, molded adsorbents may be pulverized into particles having a desired size. Also, adsorbents having different particle sizes (for example, 5 μm, 50 μm and 100 μm) may be used as admixed.

Recommendable adsorbents include the following inorganic adsorbents and the like.

Acid clay (for example, particle size=170 mesh through, specific surface area=150–300 $m^2$/g)

Activated clay (for example, particle size=80 mesh through or 170 mesh through, specific surface area=150–300 m /g)

Silica alumina (for example, particle size=80 mesh through, specific surface area=150–210 m /g)

Synthetic zeolite (for example, particle size=1–100 μm, pore size=about 3–10 angstroms)

Silicic acid (for example, particle size=1–30 μm, oil absorption=160–235 ml/100 g, specific surface area= 150–330 m /g)

Alkali metal (such as Na or K) salts of silicic acid (for example, particle size=50–200 μm, oil absorption= 160–230 ml/100 g)

Aluminum silicate (for example, particle size=5–200 μm, oil absorption=150–250 ml/100 g)

Aluminosilicate (for example, particle size=1–100 μm, oil absorption=150 to 200 ml/100 g)

Activated alumina (for example, particle size=80–250 mesh through, pore size=40–100 angstroms, specific surface area=200 to 400 $m^2$/g)

Silica (particle size=5–200 μm, pore size=20 angstroms, specific surface area=150–300 m /g)

Oil absorbing silica (particle size=1–200 μm, oil absorption=160–255 ml/100 g)

Diatomaceous earth (for example, particle size=10–100 μm, specific surface area=150–300 m /g)

The above adsorbents are all known, and can be used singly or at least two of them may be used in admixture.

The adsorbent can be used in combination with other additives, such as calcium carbonate, magnesium carbonate, or the like.

Red tide eliminating composition of the invention

The red tide eliminating composition of the invention is prepared by blending 1 to 70 wt. % (preferably 3 to 30 wt. %, in particular 5 to 30 wt. %) of the surfactant of the formula (1) with 99 to 30 wt. % (preferably 97 to 70 wt. %, in particular 95 to 70 wt. %) of the adsorbent, based on the total amount of the surfactant of the formula (1) and the adsorbent.

When the composition is prepared as a powdery product, it is preferable that the content of the surfactant is limited to 30 wt. % or less.

When the composition of the invention is applied to open-system seawater or freshwater areas, it is recommended to select a combination of a surfactant effective at a lower concentration and an adsorbent capable of reaching a desired depth in a shorter period.

Recommendable combinations are combinations of (a) an adduct of 7 to 20 moles of EO and lauric acid, myristic acid, palmitic acid, oleic acid, coconut oil fatty acid or a mixture of these acids, or a mixture of adducts of 7 to 20 moles of EO and these fatty acids, and (b) at least one adsorbent selected from the group consisting of diatomaceous earth, oil absorbing silica, aluminum silicate, synthetic zeolite and activated clay.

The composition of the invention may be made into a slurry, a powder or like form optinally using solvents, anti-caking agents or other additives.

Useful solvents include ethylene glycol, propylene glycol, polyethylene glycol, polypropylene glycol, glycerine, ethanol and the like. The solvent, when employed, is used usually in a proportion of 1 to 3 wt. % based on the red tide eliminating composition.

Useful anti-caking agents include sodium toluenesulfonate, sodium benzenesulfonate, sodium phenolsulfonate and the like. The anti-caking agent, when employed, is used usually in a proportion of 1 to 3 wt. % based on the red tide eliminating composition.

The composition of the invention can be prepared by mixing the components (a) and (b), together with other components optionally employed, unitl the mixture becomes a homogeneous mixture.

The mixing can be carried out by feeding the adsorbent to a conventional mixing device such as a powder mixing apparatus equipped with a thermometer and an agitating blade, adding the surfactant and if desired anti-caking agent and the like, and mixing the components. Alternatively, the composition may be prepared by feeding a solution of the surfactant in a solvent such as an alcohol, after or at the time of feeding the adsorbent, mixing the components and evaporating the solvent with heating under reduced pressure.

Usually, the red tide eliminating composition of the invention thus obtained is provided in the form of a powder. The powdery composition may take a form ranging from particles of substantially the same size as that of the adsorbent particles used, to agglomerates formed from some particles which have agglomerated. The particle size of the composition of the invention is not limited insofar as the composition has a fluidity sufficient to be spread over or injected into seawater or freshwater with a dipper or a spreader. Generally, a particle size of about 1 $\mu$m to about 2 mm, preferably about 30 $\mu$m to about 1 mm is recommended.

Method for eliminating red tide

The composition of the invention is spread over seawater or freshwater areas where red tide occurs. Usually, when the composition is sprinkled over the surface of the water, it substantially evenly reaches a depth of about 4 to 7 m where red tide planktons are present.

The red tide eliminating composition of the invention can be used in the form of a powder or a fluid (such as an aqueous dispersion or an aqueous slurry). The form of the composition can be selected according to the purpose. For example, Chattonella moves down in the sea at night but gathers in the vicinity of the sea surface in the daytime. The composition of the invention, when scattered over the sea surface, may be scattered with a dipper or a spreader, or may also be scattered from a helicopter. If planktons heavily concentrate in the sea, the red tide planktons can be eliminated more effectively by injecting the composition in the form of a fluid into water slightly above the desired depth, using a nozzle connected with a tank or the like via a pipe.

When the composition of the invention is to be used for eliminating red tide planktons in small areas, usually the powder composition as such is spread with a dipper, a spreader or other means. For treating large areas, the composition of the invention may be made into a fluid (such as an aqueous dispersion or an aqueous slurry) containing about 0.5 to 20 wt. %, preferably about 1 to 10 wt. %, of the composition of the invention, and scattered over the area to be treated using a pump or other conventional means. In this case, short-period treatment is effective.

The concentration of the composition of the invention to be dispersed in the sea is determined by calculating the amount of the red tide eliminating composition required for treating the red tide-affected area, and the composition is applied in an amount calculated considering safety factor (2 to 7 times).

More specifically, a water sample is taken from the red ride-affected area to experimentally find the minimum surfactant concentration required to destroy plankton cells in the sample. Then, the required amount of the red tide eliminating composition is calculated from said minimum surfactant concentration, volume of seawater in the red tide-affected area and content of the present surfactant in the red tide eliminating composition. Considering that the red tide eliminating composition tends to be rapidly diffused by the effect of wave or wind in fresh water and sea water, the red tide eliminating composition is used in an amount of 2 to 7 times larger than the calculated required amount, as safety factor.

EXAMPLES

Examples are given below to illustrate the present invention in detail. The following methods were employed to evaluate the following properties of the compositions.

(i) Cytocidal activity test 90 ml each of aqueous solutions of the surfactant with various concentrations was placed in a 200-ml culture bottle. To the solution was added 10 ml of a plankton culture solution. The number of plankton cells in the culture solution was 4000 plankton cells/ml.

The bottle was allowed to stand at 20° C. for 20 minutes to determine the minimum concentration (cytocidal minimum concentration, ppm) of the surfactant required to destroy (kill) 100% of the plankton cells.

Planktons used in the test were two species, Chattonella (P1) and Gymnodinium (P2).

(ii) Rate of descending

A polyethylene tube having a diameter of 24 mm and a length of 4 m was stoppered at the lower end, fixed as a whole, and filled with seawater from the upper end. Then, the red tide eliminating composition was placed into the tube from the upper end, and 3.5 minutes later, the depth (cm) reached by the sample was determined.

(iv) Uniform dispersibility and concentration distribution of surfactant

The above mentioned tube was filled with seawater to a level of 4 m. The surfactant at a concentration (hereinafter referred to as "set concentration"), which was 2 to 4 times higher than the cytocidal minimum concentration determined in (i) above, was scattered on the water surface, considering the safety factor of 2 to 4 times.

30 minutes later, the surfactant concentrations at depths of 1 m, 2 m and 4 m were determined by the ammonium cobalt thiocyanate method. Also, Chattonella (4,000 cells/ml) was uniformly dispersed throughout the seawater and checked for survival of the cells.

(v) Aquatic toxicity

Two young yellowtails with a length of 17 cm and four horse mackerels with a length of 12 cm were allowed to swim in a tank filled with 40 liters of seawater at 25° C. containing Chattonella in an amount usually fatal to fish (4,000 cells/ml), while slowly blowing air into the seawater. A predetermined amount of the red tide eliminating composition was placed into the tank, which was then allowed to stand at 25° C. for 24 hours. Thereafter, it was checked whether the planktons and fishes were alive or dead.

The amount of the red tide eliminating composition used in each Example was selected such that the concentration of the surfactant released in the seawater would become identical to the set concentration.

(vi) Powder properties of the composition

A powder obtained by uniformly mixing the surfactant and the adsorbent was allowed to stand at 40° C. for 3 months. Thereafter, the powder properties (occurrence of caking and fluidity) of the powder were observed with time, and an overall evaluation was made on the following scale.
◯: Good (no caking, having fluidity)
Δ: Unsatisfactory (slight caking, insufficient fluidity)
×: Poor (appreciable caking, no fluidity)

Examples 1 to 22

Red tide eliminating compositions having the make-ups shown in Tables 1 to 3 were prepared.

Each composition was prepared in the following manner, using the surfactant and adsorbent in the proportion shown in Tables 1 to 3. That is, the surfactant was dissolved in ethanol, and the resulting solution and the adsorbent were placed in a powder mixing apparatus, stirred and heated. Ethanol was then evaporated off at 70° C. under reduced pressure. The residue was cooled to room temperature, giving a red tide eliminating composition in the form of a powder having good uniformity.

In Table 1, the surfactants are expressed in terms of the kinds of the fatty acids and the kinds of the alkylene oxides constituting the surfactants, and the number of moles of the alkylene oxides added (the same applies to Tables 2 to 4).

The adsorbents used have the following particle size, oil absorption (as determined according to JIS K 6220-1977), specific surface area and pore size.

| Adsorbent | Particle size ($\mu$m) | Other physical properties |
|---|---|---|
| Activated clay | 70 | Specific surface area: 200 $m^2/g$ |
| Diatomaceous earth | 50 | Specific surface area: 200 $m^2/g$ |
| Synthetic zeolite | 100 | Pore size: 10 Å |
| Oil absorbing silica | 40 | Oil absorption: 250 ml/100 g |
| Sodium silicate | 100 | Oil absorption: 200 ml/100 g |
| Silica | 30 | Pore size: 20 Å |
| Acid clay | 80 | Specific surface area: 300 $m^2/g$ |
| Aluminum silicate | 50 | Oil absorption: 250 ml/100 g |
| Activated alumina | 150 | Pore diameter: 100 Å |
| Silica alumina | 120 | Specific surface area: 210 $m^2/g$ |

First, the cytocidal minimum concentration of the surfactant alone, which was the same surfactant as used for preparing the composition, was determined.

Subsequently, the reached depth, surfactant concentration, aquatic toxicity (to the fishes and planktons) and powder properties of the red tide eliminating compositions shown in Tables 1 to 3 were determined and evaluated. The results are shown in Tables 1 to 3.

In Table 1, "D" stands for "dead", and "L" stands for "living" (the same applies to Tables 2 to 4).

TABLE 1

| | Example | | | | | | | | | |
|---|---|---|---|---|---|---|---|---|---|---|
| | 1 | 2 | 3 | 4 | 5 | 6 | 7 | 8 | 9 | 10 |
| Surfactant (wt. %) | | | | | | | | | | |
| Lauric acid EO8 | 9 | | | | | | | | | |
| Myristic acid EO10 | | 5 | | | | | | | | |
| Palmitic acid EO16 | | | 17 | | | | | | | |
| Oleic acid EO15 | | | | 15 | | | | | | |
| Stearic acid EO30 | | | | | 70 | | | | | |
| Isostearic acid EO14 | | | | | | 10 | | | | |
| Lauric acid PO2EO25 | | | | | | | 40 | | | |
| Linolic acid EO15 | | | | | | | | 25 | | |
| Fatty acid mixture a EO12 | | | | | | | | | 10 | |
| Fatty acid mixture b EO18 | | | | | | | | | | 30 |
| Adsorbent (wt. %) | | | | | | | | | | |
| Activated clay | 91 | | | | | | | | | |
| Diatomaceous earth | | 95 | | | | | | | | |
| Synthetic zeolite | | | 20 | | | | | | | |
| Oil absorbing silica | | | 63 | | | | | | | |
| Sodium silicate | | | | 85 | | | | | | |
| Silica | | | | | 30 | | | 75 | | |
| Acid clay | | | | | | 90 | | | | |
| Aluminum silicate | | | | | | | 60 | | | |
| Activated alumina | | | | | | | | | 90 | |
| Silica alumina | | | | | | | | | | 70 |

| | Example | | | | | | | | | |
|---|---|---|---|---|---|---|---|---|---|---|
| | 1 | 2 | 3 | 4 | 5 | 6 | 7 | 8 | 9 | 10 |

TABLE 1-continued

| Cytocidal minimum concentration (ppm) | | | | | | | | | | |
|---|---|---|---|---|---|---|---|---|---|---|
| P1 | 7 | 5 | 6 | 4 | 35 | 10 | 30 | 6 | 5 | 15 |
| P2 | 9 | 5 | 8 | 5 | 35 | 12 | 35 | 6 | 6 | 18 |
| Reached depth (cm) | 130 | 250 | 120 | 150 | 120 | 160 | 200 | 130 | 150 | 140 |
| Surfactant concentration (ppm) | | | | | | | | | | |
| 1 m | 17 D | 8 D | 18 D | 7 D | 45 D | 15 D | 40 D | 10 D | 9 D | 20 D |
| 2 m | 19 D | 7 D | 20 D | 7 D | 40 D | 20 D | 38 D | 12 D | 10 D | 22 D |
| 4 m | 20 D | 8 D | 22 D | 7 D | 43 D | 17 D | 42 D | 12 D | 12 D | 23 D |
| Aquatic toxicity test | | | | | | | | | | |
| Fish | L | L | L | L | L | L | L | L | L | L |
| Plankton | D | D | D | D | D | D | D | D | D | D |
| Powder properties | ○ | ○ | ○ | Δ | Δ | ○ | ○ | X | ○ | ○ |

Fatty acid mixture a: fatty acid mixture of oleic acid/palmitic acid (30/70; on a weight basis)
Fatty acid mixture b: fatty acid mixture of oleic acid/myristic acid (40/60; on a weight basis)

TABLE 2

| | Example | | | |
|---|---|---|---|---|
| | 11 | 12 | 13 | 14 |
| Coconut oil fatty acid EO10 | 15 | | 12 | |
| Lauric acid EO12 | | 14 | | |
| Palmitic acid EO14 | | | 6 | |
| Myristic acid EO14 | | | | 8 |
| Lauric acid EO8 | | | | 15 |
| Stearic acid EO30 | | | | 15 |
| Synthetic zeolite | 85 | | | |
| Diatomaceous earth | | 80 | | |
| Activated clay | | | 70 | |
| Silica | | | | 80 |
| Cytocidal minimum concentration (ppm) | | | | |
| P1 | 10 | 5 | 7 | 16 |
| P2 | 14 | 6 | 8 | 19 |
| Reached depth (cm) | 150 | 200 | 150 | 170 |
| Surfactant concentration (ppm) | | | | |
| 1 m | 20 D | 20 D | 22 D | 15 D |
| 2 m | 25 D | 25 D | 25 D | 20 D |
| 4 m | 30 D | 27 D | 35 D | 25 D |
| Aquatic toxicity test | | | | |
| Fish | L | L | L | L |
| Plankton | D | D | D | D |
| Powder properties | ○ | ○ | ○ | ○ |

TABLE 3

| | Example | | | | | | | |
|---|---|---|---|---|---|---|---|---|
| | 15 | 16 | 17 | 18 | 19 | 20 | 21 | 22 |
| Surfactant (wt. %) | | | | | | | | |
| Myristic acid EO12 | 20 | | | | | 14 | 15 | |
| Myristic acid EO14 | | 30 | | | | | | |
| Oleic acid | | | 10 | | | | | |
| EO12 | | | | | | | | |
| Oleic acid EO14 | | | | | 12 | | 6 | |
| Lauric acid EO9 | | | | 25 | | | | 15 |
| Palmitic acid EO14 | | | | | | | | 25 |
| Adsorbent (wt. %) | | | | | | | | |
| Activated clay | | 35 | 90 | | | | | 30 |
| Synthetic zeolite | 40 | | | | 75 | | 49 | 45 |
| Oil absorbing silica | | | | 88 | | | | |
| Diatomaceous earth | 40 | | | | | 80 | | |
| Aluminum silicate | | 35 | | | | | 21 | |
| Cytocidal minimum concentration (ppm) | | | | | | | | |
| P1 | 4 | 4 | 4 | 4 | 6 | 4 | 4 | 6 |
| P2 | 4 | 4 | 4 | 7 | 4 | 4 | 5 | |
| Reached depth (cm) | 175 | 160 | 130 | 150 | 150 | 250 | 150 | 150 |
| Surfactant concentration (ppm) | | | | | | | | |
| 1 m | 7 D | 10 D | 8 D | 10 D | 9 D | 10 D | 10 D | 8 D |
| 2 m | 8 D | 8 D | 9 D | 9 D | 11 D | 8 D | 9 D | 10 D |
| 4 m | 10 D | 7 D | 11 D | 7 D | 13 D | 9 D | 7 D | 13 D |
| Aquatic toxicity test | | | | | | | | |
| Fish | L | L | L | L | L | L | L | L |
| Plankton | D | D | D | D | D | D | D | D |
| Powder properties | ○ | ○ | ○ | ○ | ○ | ○ | ○ | ○ |

Comparative Examples 1 and 2

Using only each of the surfactants listed in Table 4, the red tide plankton cytocidal minimum concentrations thereof were determined.

Subsequently, powdery red tide eliminating compositions were prepared following the procedure of Examples 1 to 22 with the exception of using the surfactants and adsorbents listed in Table 4. The reached depth, surfactant concentration, aquatic toxicity (to the fishes and planktons), and powder properties of the compositions were determined and evaluated.

The results are shown in Table 4.

Comparative Examples 3 and 4

The present surfactants shown in Table 4 were used as such. The cytocidal minimum concentration, reached depth, aquatic toxicity, surfactant concentration and powder properties of the surfactants were determined and evaluated.

The results are shown in Table 4.

Comparative Examples 5 and 6

The adsorbents shown in Table 4 were used as such. The cytocidal minimum concentration, reached depth, aquatic toxicity and powder properties of the adsorbents were determined and evaluated.

The results are shown in Table 4.

TABLE 4

| | Comparative Example | | | | | |
|---|---|---|---|---|---|---|
| | 1 | 2 | 3 | 4 | 5 | 6 |
| Surfactant (wt. %) | | | | | | |
| Capric acid EO35 | 10 | | | | | |
| Palmitic acid EO40 | | 20 | | | | |
| Lauric acid EO15 | | | 100 | | | |
| Stearic acid EO20 | | | | 100 | | |
| Adsorbent (wt. %) | | | | | | |
| Activated clay | 90 | | | | | |
| Diatomaceous earth | | | | | | 100 |
| Synthetic zeolite | | 80 | | | 100 | |
| Cytocidal minimum concentration (ppm) | | | | | | |
| P1 | 50< | 50< | 24 | 36 | 50< | 50< |
| P2 | 50< | 59< | 25 | 40 | 50< | 50< |
| Reached depth (cm) | 100 | 120 | 50> | 50> | 60 | 100 |
| Surfactant concentration (ppm) | | | | | | |
| 1 m | 50 | 36 | 100 | 200 | — | — |
| | L | L | D | D | L | L |
| 2 m | 55 | 40 | 20 | 50 | — | — |
| | L | L | L | D | L | L |
| 4 m | 58 | 40 | 5 | 10 | — | — |
| | L | L | L | L | L | L |
| Aquatic toxicity test | | | | | | |
| Fish | L | L | L | L | L | L |
| Plankton | L | L | L | L | L | L |
| Powder properties | ○ | ○ | X | X | ○ | ○ |

Tables 1 to 4 reveal the following.

Since the red tide eliminating composition of the present invention comprises a surfactant having a low cytocidal minimum concentration, it shows good red tide eliminating effect at a low concentration.

As apparent from the reached depth data, the composition of the present invention reaches the desired depth efficiently in a short period.

The composition, after being scattered, releases the surfactant at substantially the same concentration at depths of 1 m, 2 m and 4 m. That is, the composition has excellent effect of uniformly dispersing in water after being scattered, and can kill red tide planktons at depths of 1 m, 2 m and 4 m.

Moreover, the aquatic toxicity test results demonstrate that the composition of the invention has substantially no appreciable adverse effect on fish but can effectively eliminate red tide planktons.

What is claimed is:

1. A red fide eliminating composition comprising:

(a) at least one (polyoxyalkylene) fatty acid ester represented by the formula (1)

$$RCOO(AO)nH \qquad (1)$$

wherein R is a $C_{7-22}$ alkyl or alkenyl group, n is an integer of 1 to 30 and AO is a $C_{2-4}$ alkylene oxide, and (b) at lease one powdery adsorbent;

wherein, based on the total weight of said at least one (polyoxyalkylene) fatty acid ester (a) represented by the formula (1) and said at least one absorbent (b), said at least one (polyoxyalkylene) fatty acid ester (a) represented by the formula (1) is present in an amount of 1 to 70 wt. % and said at least one adsorbent (b) is present in an amount of 99 to 30 wt. %;

and wherein the red tide eliminating composition is in the form of a homogeneous mixture of components (a) and (b).

2. The composition according to claim 1 wherein R is a $C_{8-22}$ alkyl or alkenyl group.

3. The composition according to claim 1 wherein in the formula (1) R represents a $C_{11-17}$ alkyl or alkenyl group, n represents an integer of 7 to 20, and AO represents ethylene oxide.

4. The composition according to claim 1 wherein the (polyoxyalkylene) fatty acid ester of the formula (1) is at least one member selected from the group consisting of ethylene oxide adducts of lauric acid (the number of moles of ethylene oxide added=1 to 30), ethylene oxide adducts of myristic acid (the number of moles of ethylene oxide added=1 to 30), ethylene oxide adducts of palmitic acid (the number of moles of ethylene oxide added=1 to 30), ethylene oxide adducts of oleic acid (the number of moles of ethylene oxide added=1 to 30) and ethylene oxide adducts of isostearic acid (the number of moles of ethylene oxide added=1 to 30).

5. The composition according to claim 1 wherein the (polyoxyalkylene) fatty acid ester of the formula (1) is at least one member selected from the group consisting of ethylene oxide adducts of lauric acid (the number of moles of ethylene oxide added=1 to 30), ethylene oxide adducts of myristic acid (the number of moles of ethylene oxide added=1 to 30), ethylene oxide adducts of palmitic acid (the number of moles of ethylene oxide added=1 to 30), ethylene oxide adducts of oleic acid (the number of moles of ethylene oxide added=1 to 30), ethylene oxide adducts of isostearic acid (the number of moles of ethylene oxide added=1 to 30) and ethylene oxide adducts of coconut oil fatty acid (the number of moles of ethylene oxide added=1 to 30).

6. The composition according to claim 1 wherein the (polyoxyalkylene) fatty acid ester of the formula (1) is:

(polyoxyethylene) myristic acid ester (the number of moles of ethylene oxide added=12 or 14), (polyoxyethylene) oleic acid ester (the number of moles of ethylene oxide added=12 or 14) (polyoxyethylene) lauric acid ester (the number of moles of ethylene oxide added=9)

(polyoxyethylene) palmitic acid ester (the number of moles of ethylene oxide added=14)

(polyoxyethylene) coconut oil fatty acid ester (the number of moles of ethylene oxide added=10)

a mixture of 30 wt. % of (polyoxyethylene) oleic acid ester (the number of moles of ethylene oxide added=14) and 70 wt. % of (polyoxyethylene) myristic acid ester (the number of moles of ethylene oxide added=14), or a mixture of 50 wt. % of (polyoxyethylene) lauric acid ester (the number of moles of ethylene oxide added=9) and 50 wt. % of (polyoxyethylene) myristic acid ester (the umber of moles of ethylene oxide added=12).

7. The composition according to claim 1 wherein, based on the total weight of said at least one (polyoxyalkylene) fatty acid ester (a) represented by the formula (1) and said at least one adsorbent (b), said at least one (polyoxyalkylene) fatty acid ester (a) represented by the formula (1) is present in an amount of 5 to 30 wt. % and said at least one adsorbent (b) is present in an amount of 95 to 70 wt. %.

8. The composition according to claim 1 wherein the adsorbent (b) is at least one member selected from the group consisting of acid clay, activated clay, silica alumina, synthetic zeolite, silicic acid, sodium silicate, aluminum silicate, aluminosilicate, activated alumina, silica, oil absorbing silica and diatomaceous earth.

9. The composition according to claim 1 wherein the adsorbent (b) is activated clay, synthetic zeolite, oil absorbing silica or diatomaceous earth, or is a mixture of 50 wt. % of synthetic zeolite and 50 wt. % of diatomaceous earth, or a mixture of 50 wt. % of activated clay and 50 wt. % of aluminum silicate.

10. The composition according to claim 1 wherein the adsorbent (b) has a particle size of 1 to 200 μm.

11. The composition according to claim 1 wherein the adsorbent (b) has at least one physical property selected from the group consisting of:

a) an oil absorption (as determined according to JIS K 6220-1977) of 150 ml or more, preferably 160 to 250 ml, per 100 g of the adsorbent, b) a specific surface area of 150 m$^2$/g or more, preferably 200 to 400 m$^2$/g, and c) a pore size of 3 to 100 angstroms, preferably 3 to 20 angstroms.

12. A method for eliminating red tide characterized in that it comprises scattering or introducing a red fide eliminating composition over or into seawater or freshwater affected with red tide, the composition comprising:

(a) at least one (polyoxyalkylene) fatty acid ester represented by the formula (1)

$$RCOO(AO)nH \quad (1)$$

wherein R is a $C_{7-22}$ alkyl or alkenyl group, n represents an integer of 1 to 30 and AO represents a $C_24$ alkylene oxide, and (b) at lease one powdery adsorbent;

wherein, based on the total weight of said at least one (polyoxyalkylene) fatty acid ester (a) of the formula (1) and said at least one absorbent (b), said at least one (polyoxyalkylene) fatty acid ester (a) of the formula (1) is present in an amount of 1 to 70 wt. % and said at least one adsorbent (b) is present in an amount of 99 to 30 wt. %; and wherein the red tde eliminating composition is in the form of a homogeneous mixture of components (a) and (b).

13. The method according to claim 12 wherein the red tide eliminating composition is scattered over the surface of the water.

14. The method according to claim 12 wherein the red tide eliminating composition is introduced into the water.

15. The method according to claim 12 wherein R is a $C_{8-22}$ alkyl or alkenyl group.

16. The method according to claim 12 wherein R represents a $C_{11-17}$ alkyl or alkenyl group, n represents an integer of 7 to 20 and AO represents ethylene oxide.

17. The method according to claim 12 wherein the (polyoxyalkylene) fatty acid ester of the formula (1) is at least one member selected from the group consisting of ethylene oxide adducts of lauric acid (the number of moles of ethylene oxide added=1 to 30), ethylene oxide adducts of myristic acid (the number of moles of ethylene oxide added=1 to 30), ethylene oxide adducts of palmitic acid (the number of moles of ethylene oxide added=1 to 30), ethylene oxide adducts of oleic acid (the number of moles of ethylene oxide added=1 to 30) and ethylene oxide adducts of isostearic acid (the number of moles of ethylene oxide added=1 to 30).

18. The method according to claim 12 wherein the (polyoxyalkylene) fatty acid ester of the formula (1) is at least one member selected from the group consisting of ethylene oxide adducts of lauric acid (the number of moles of ethylene oxide added=1 to 30), ethylene oxide adducts of myristic acid (the number of moles of ethylene oxide added=1 to 30), ethylene oxide adducts of palmitic acid (the number of moles of ethylene oxide added=1 to 30), ethylene oxide adducts of oleic acid (the number of moles of ethylene oxide added=1 to 30), ethylene oxide adducts of isostearic acid (the number of moles of ethylene oxide added=1 to 30) and ethylene oxide adducts of coconut oil fatty acid (the number of moles of ethylene oxide added=1 to 30).

19. The method according to claim 12 wherein the (polyoxyalkylene) fatty acid ester of the formula (1) is:

(polyoxyethylene) myristic acid ester (the number of moles of ethylene oxide added=12 or 14), (polyoxyethylene) oleic acid ester (the number of moles of ethylene oxide added=12 or 14)

(polyoxyethylene) lauric acid ester (the number of moles of ethylene oxide added=9)

(polyoxyethylene) palmitic acid ester (the number of moles of ethylene oxide added=14)

(polyoxyethylene) coconut oil fatty acid ester (the number of moles of ethylene oxide added=10)

a mixture of 30 wt. % of (polyoxyethylene) oleic acid ester (the number of moles of ethylene oxide added=14) and 70 wt. % of (polyoxyethylene) myristic acid ester (the number of moles of ethylene oxide added=14), or a mixture of 50 wt. % of (polyoxyethylene) lauric acid ester (the number of moles of ethylene oxide added=9) and 50 wt. % of (polyoxyethylene) myristic acid ester (the number of moles of ethylene oxide added=12).

20. The method according to claim 12 wherein, based on the total weight of said at least one (polyoxyalkylene) fatty acid ester (a) represented by the formula (1) and said at least one adsorbent (b), said at least one (polyoxyalkylene) fatty acid ester (a) represented by the formula (1) is present in an amount of 5 to 30 wt. % and said at least one adsorbent (b) is present in an amount of 95 to 70 wt. %.

21. The method according to claim 12 wherein the adsorbent (b) is at least one member selected from the group consisting of acid clay, activated clay, silica alumina, synthetic zeolite, silicic acid, sodium silicate, aluminum silicate, aluminosilicate, activated alumina, silica, oil absorbing silica and diatomaceous earth.

22. The method according to claim 12 wherein the adsorbent (b) is activated clay, synthetic zeolite, oil absorbing silica or diatomaceous earth, or is a mixture of 50 wt. % of synthetic zeolite and 50 wt. % of diatomaceous earth, or a mixture of 50 wt. % of activated clay and 50 wt. % of aluminum silicate.

23. The method according to claim 12 wherein the adsorbent (b) has a particle size of 1 to 200 μm.

24. The method according to claim 12 wherein the adsorbent (b) has at least one physical property selected from the group consisting of:
   a) an oil absorption (as determined according to JIS K 6220-1977) of 150 ml or more, preferably 160 to 250 ml, per 100 g of the adsorbent,
   b) a specific surface area of 150 m /g or more, preferably 200 to 400 m /g, and
   c) a pore size of 3 to 100 angstroms, preferably 3 to 20 angstroms.

* * * * *